(12) United States Patent
Hendrick et al.

(10) Patent No.: US 7,146,894 B2
(45) Date of Patent: Dec. 12, 2006

(54) AUTOMATED MICROTOME BLADE CHANGER

(75) Inventors: Kendall B. Hendrick, Tucson, AZ (US); Darin McDaniel, Tucson, AZ (US); Miroslav Holubec, Tucson, AZ (US); William Richards, Tucson, AZ (US); Vincent Rizzo, Tucson, AZ (US)

(73) Assignee: Ventana Medical Systems, Inc., Tucson, AZ (US)

( * ) Notice: Subject to any disclaimer, the term of this patent is extended or adjusted under 35 U.S.C. 154(b) by 20 days.

(21) Appl. No.: 09/844,833

(22) Filed: Apr. 27, 2001

(65) Prior Publication Data

US 2002/0005104 A1    Jan. 17, 2002

Related U.S. Application Data

(63) Continuation-in-part of application No. 09/562,270, filed on Apr. 29, 2000, now abandoned.

(51) Int. Cl.
*B26D 7/26* (2006.01)

(52) U.S. Cl. ............... 83/703; 83/698.11; 83/915.5; 83/954

(58) Field of Classification Search ............... 83/915.5, 83/954, 698.11, 76.9, 703, 629, 628, 613, 83/651, 627; 483/10, 1
See application file for complete search history.

(56) References Cited

U.S. PATENT DOCUMENTS

| | | | |
|---|---|---|---|
| 1,817,512 A | 8/1931 | Gaisman | |
| 2,592,138 A | 4/1952 | Gwoosh et al. | |
| 2,604,979 A | 7/1952 | Roberts | |
| 2,653,379 A | 9/1953 | Austin | |
| 2,679,685 A | 6/1954 | Austin | |
| 2,741,837 A | 4/1956 | Breazeale | |
| 2,775,366 A | 12/1956 | Willhelm | |
| 3,667,330 A | 6/1972 | Kobernick | |
| 3,751,858 A | 8/1973 | Schaller et al. | |
| 3,871,077 A | 3/1975 | Nissen et al. | |
| 4,207,790 A | 6/1980 | Endo | |
| 4,700,600 A * | 10/1987 | Pickett | 83/165 |
| 5,099,735 A * | 3/1992 | Kempe et al. | 83/699.61 |
| 5,409,133 A | 4/1995 | Gringer | |
| 5,461,953 A * | 10/1995 | McCormick | 83/36 |
| 5,937,522 A * | 8/1999 | Althaus et al. | 30/40.2 |
| 6,030,326 A * | 2/2000 | Azuma et al. | 483/31 |
| 6,651,538 B1 * | 11/2003 | Tamura et al. | 83/575 |

\* cited by examiner

*Primary Examiner*—Boyer D. Ashley
*Assistant Examiner*—Omar Flores Sánchez
(74) *Attorney, Agent, or Firm*—Huw R. Jones (57) ABSTRACT

An automated rotary microtome blade changing apparatus, comprising an upper stage being adapted to releasably engage a supply cartridge and a waste cartridge, the upper stage having a loading segment adapted to engage and move blades contained within the supply cartridge into a cutting position; clamping means for releasably holding the blades in place for cutting operations; power means for driving the movement of blades and clamping mechanisms; and electronic control means for integrating all of the functions of the apparatus.

2 Claims, 8 Drawing Sheets

AUTOMATED MICROTOME BLADE CHANGER

RELATED APPLICATIONS

This application is a continuation-in-part of commonly assigned U.S. Ser. No. 09/562,270, filed Apr. 29, 2000 now abandoned.

BACKGROUND

1. Field of the Invention

The present invention is directed to apparatus for use in preparing tissue sections for use in diagnostic histopathology and, more particularly, to an apparatus that automatically changes the blades of a microtome without exposure of the user to the cutting edges of the blades.

2. Description of Related Art

Microtomes have been used for many years to meet the exacting requirements necessary for thin sectioning of paraffin-embedded tissue. Essentially, microtomes are holders for razor-sharp metal blades, against which a block of paraffin-embedded tissue is moved in an up-and-down motion. Concurrently, either the tissue block is advanced against the blade, or vice versa, so that with each up or down stroke, a thin slice or "section" of tissue is cut from the block. The blades are highly engineered for the precise requirements of tissue sectioning. Specifically, the blades are capable of cutting sections as thin as 1 μm.

The present practice for tissue sectioning requires the blades be changed as they become dulled. This necessitates alleviating the pressure that the blade holder puts on the blade to keep it in place, usually be removing a clamping mechanism. Once the clamp is removed, the blade can be lifted off of the rest. Usually, this is accomplished by grasping the blade at an edge and discarding it in a sharps container, all of which is done by hand. This exposed the user to the edges of the blade, and of course the potential of serious injury. Additional exposure to the sharp blade occurs when loading a new blade and re-clamping it in position.

U.S. Pat. No. 3,667,330 (Kobernick) discloses an automated microtome assembly which includes a continuous flexible steel blade whose ends are mounted upon feed and takeup reels for intermittent motor-driven advancement to enable advancement of new cutting surface without contact by a user. The changing of the knife edge may be actuated manually or automatically. The '330 patent does not disclose a method or apparatus for the changing of individual blades, or provide safety features for the changing of the blade.

U.S. Pat. No. 4,207,790 (Endo) is directed to a knife holder and blade cassette for microtomes. The knife holder comprises a base plate and a holder plate for holding the knife edge onto the base plate. The blade cartridge is spring-loaded for biasing the blades upwardly towards the exit from the cartridge. To replace a blade, the user must first loosen the bolts holding the knife holder plate down, then engage the cartridge with the edge of the knife holder assembly, and finally slide a new blade out of the cartridge and into contact with the dull blade, thereby positioning a new blade beneath the holder plate and simultaneously pushing the dull blade out of position. There is no disclosure related to automation of the process, what happens to the spent blade, or safety features.

Blade changers for hand-held shavers are known. U.S. Pat. No. 1,817,512 (Gaisman) and U.S. Pat. No. 2,741,837 (Breazeale) disclose a cartridge containing individual blades wherein the blade is manually dispensed from the cartridge using an ejector, and at the end of the ejector stroke the blade is located in the cutting position, and the used blade is received in a take-up cartridge (see Gaisman, FIG. 11). U.S. Pat. No. 2,653,379 (Austin) discloses a box with a cartridge on either side of a razor. A slider pushes a new blade from the first cartridge onto the razor, which pushes the used blade into the second cartridge. U.S. Pat. No. 2,679,685 (Austin) discloses a razor blade changer where advancing a pusher causes a blade in supply cartridge C to advance into the razor and push the used blade out into take-up cartridge D. When cartridge C is empty, it is put in place of discarded cartridge D to act as the new take-up cartridge, and a full supply cartridge is put in place of cartridge C.

Patents on razor blade containers include U.S. Pat. No. 2,592,138 (Gwoosh et al.) for a razor blade package which teaches the use of a coil spring to bias blades towards the dispenser opening of a blade container. The top has a thumb opening to allow manual advance of the blades. U.S. Pat. No. 2,604,979 Roberts) shows a spring-loaded blade container which uses a leaf-spring U.S. Pat. No. 2,775,366 (Willhelm) discloses the use of a compression spring to urge a plurality of blades towards the package opening. U.S. Pat. No. 5,409,133 (Gringer) is a spring-loaded blade dispenser wherein the entire top except guide rails, is open for application of a manual dispensing force. The dispenser is also capable of receiving spent blades back through a disposal opening 34 (see FIGS. 9–10). None of the above mentioned patents are adapted for automatic use.

There is a need for an automated microtome blade changing system that safeguards the user against being seriously injured, and enhances the work flow in the pathology laboratory.

SUMMARY OF THE INVENTION

The invention is directed to an automated rotary microtome blade changing apparatus, comprising an upper stage adapted to releasably engage a supply and a waste cartridge, the upper stage having a loading segment adapted to engage and move blades contained within said supply cartridge into a cutting position; clamping means for releasably holding the blades in place for cutting operations; power means for driving the movement of blades and clamping mechanisms; and electronic control means for integrating all of the functions of the apparatus.

The invention is also directed to an automated rotary microtome blade changing apparatus, comprising an upper stage adapted to releasably engage a supply and a waste cartridge, the upper stage having a reverser shuttle adapted to engage and move blades contained within said supply cartridge into a cutting position; clamping means for releasably holding the blades in place for cutting operations; power means for driving the movement of blades and clamping mechanisms; and electronic control means for integrating all of the functions of the apparatus.

Also described herein is an improved blade supply cartridge wherein the cartridge comprises a body, a spring, a dispensing tab, and blades, wherein the improvement comprises a toothed portion on said dispensing tab adapted to engage mating gear teeth on said blade changer.

Also described herein is an improved blade supply cartridge wherein the cartridge comprises a body, a spring, a dispensing tab, and blades, wherein the improvement comprises a touch memory device in contact with the cartridge, the touch memory device programmed to contain content information relating to said cartridge.

It is an object of the present invention to provide a fully automated blade changer for the histopathology laboratory that reduces and hopefully eliminates the chances of being cut accidentally during routine laboratory operations with the microtome blades.

It is another object of the present invention to provide a new blade cartridge that, in cooperation with a microcontroller in the blade changer, can track blade useage and signal the user when blades are running low.

These and other advantages of the present invention will become clear in the following description of the invention.

DESCRIPTION OF THE PREFERRED EMBODIMENTS

The purpose of this invention is to improve the safety and productivity of the process of cutting tissue blocks with a rotary microtome. It is achieved by automating the process of loading new knife blades into the microtome and disposing of used ones. At present, cutting tissue on a microtome involves considerable handling of disposable knife blades with the technologist's bare hand. So, because the edge of the blade is razor sharp, cutting injuries are common. This risk of injury is significant even if the technologist only comes into contact with a blade twice—once to load, once to discard—but current practice in histotechnology often greatly increases this exposure.

There are two other problems the invention ameliorates. First, with constant handling of the blade also comes a risk of infection from the tissue. With properly processed tissue there is no risk of infection, but it is possible with non-processed or under-processed tissue that direct contact with the tissue can lead to infection. Therefore, by eliminating all physical contact with the blade, the risk of infection is significantly reduced. Secondly, the process of loading and unloading the blades by hand is somewhat time-consuming. The invention addresses this issue as well, by replacing the manual movement of blades with an automated movement of blades.

Thus, this invention offers to the histology laboratory increased safety, flexibility and efficiency. These features all translate to the laboratory's financial bottom line: safety translates to fewer missed work days and enhanced risk management, while flexibility and efficiency allow the laboratory to provide a maximum output of staining results with a minimum number of laboratory technicians.

Figure 1:
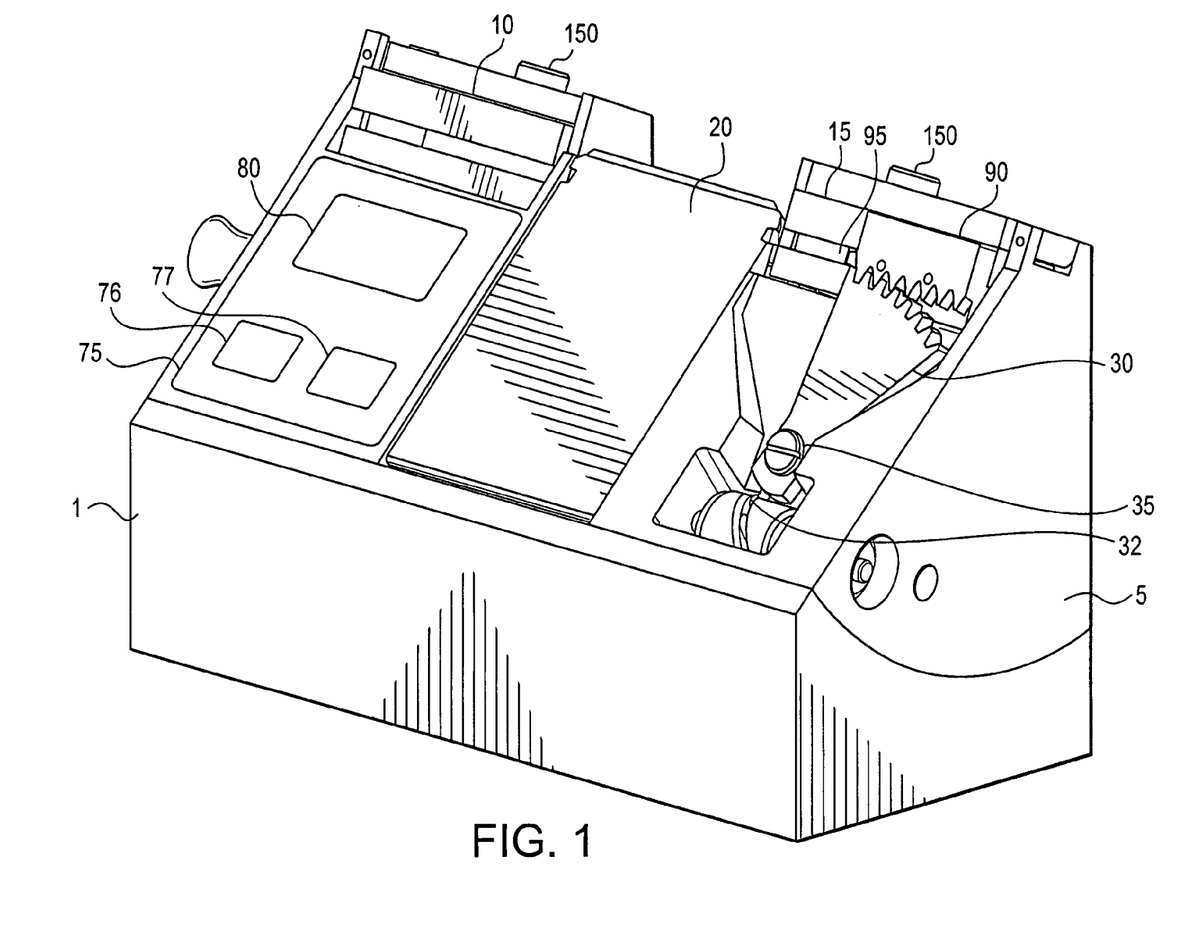
FIG. 1 is a front elevational view of the automated blade changer with both the upper and lower stages shown.
Figure 2:
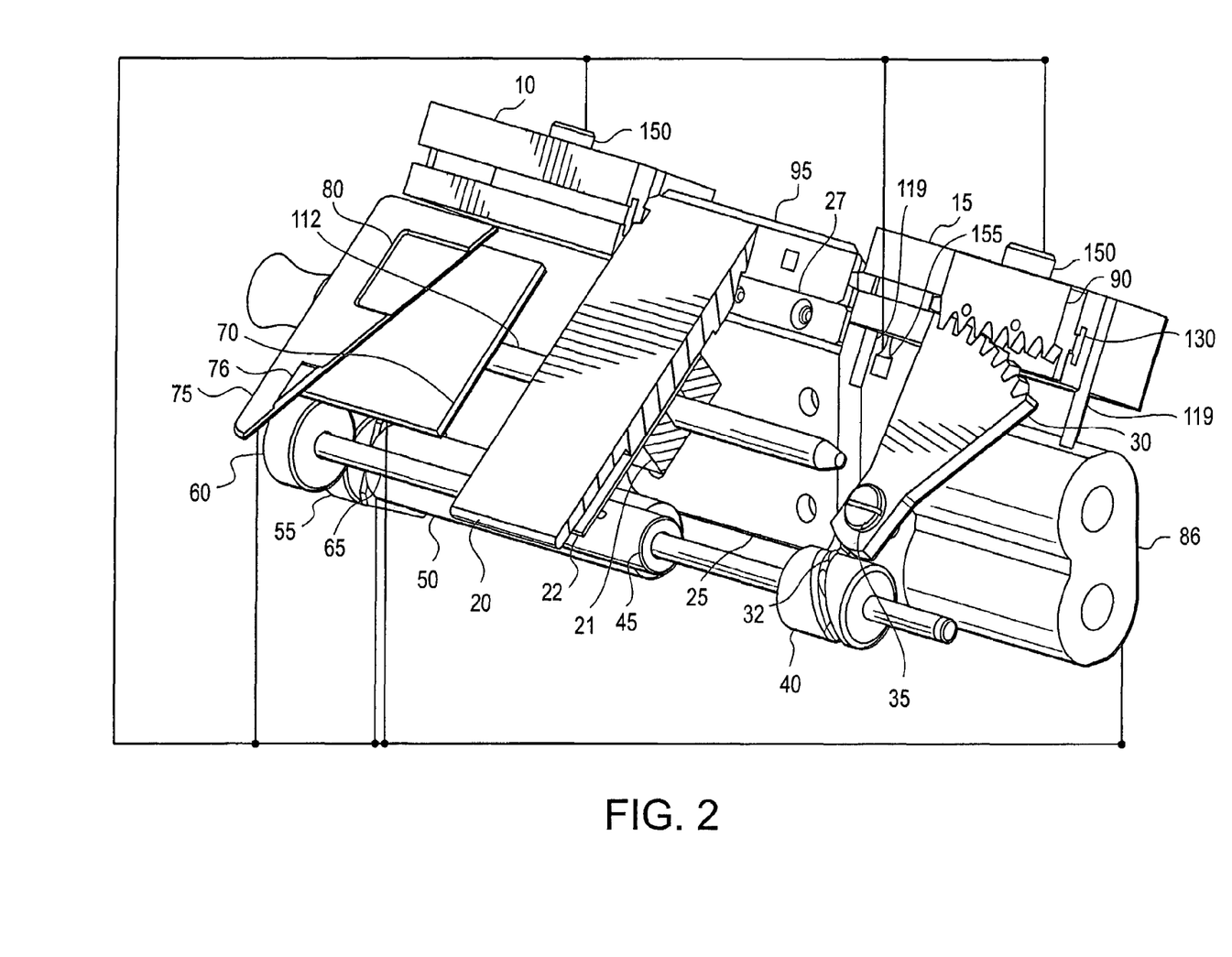
FIG. 2 is a front elevational view with partial cutaway of the upper stage of the device.
Figure 3A:
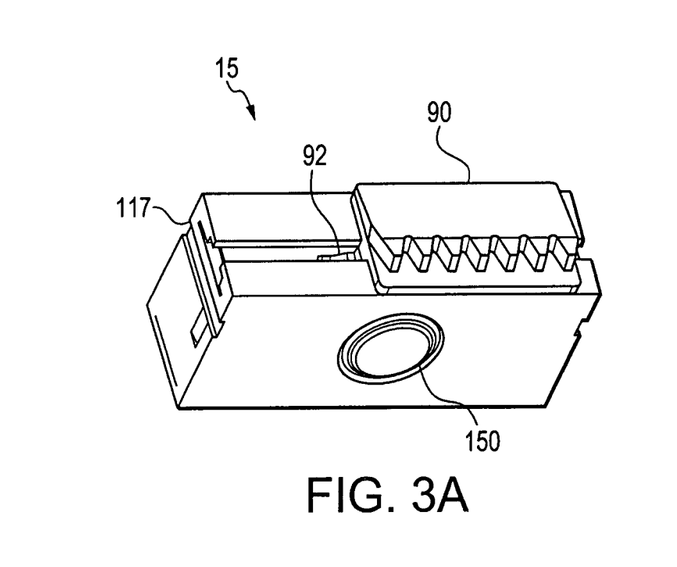
FIGS. 3A–3D show, respectively, a perspective view of a blade supply cartridge, a top view of the same, a sectional view along lines C—C shown in 3B, and a blade adapted for use with the invention.
Figure 3B:
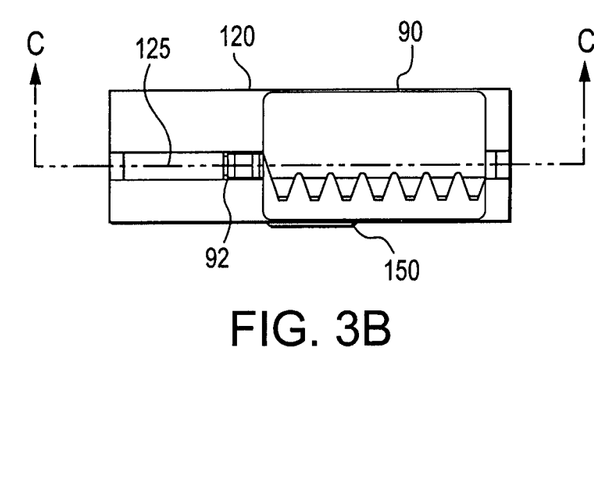
Figure 3C:
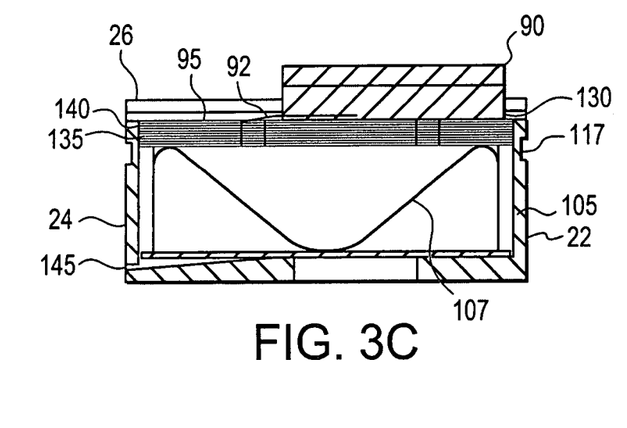
Figure 3D:
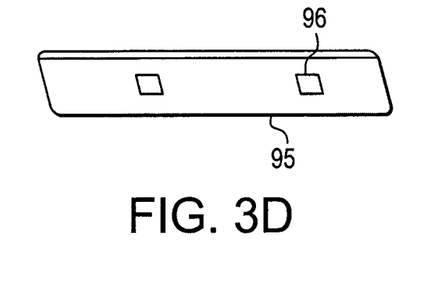

The invention is best illustrated by reference to the following FIGS. 1–2. The preferred embodiments are based on a standard knife stage design. That is, the invention is contained within the upper stage body of a standard rotary microtome knife holder. In FIGS. 1 and 2, the upper stage body 5 is the platform for the functional portions of the blade changer apparatus. It contains the major sub-components of the blade changer, including waste and supply blade cartridges 10, 15, respectively, clamping means, blade 100, power means and electronic control means. A general overview of the device follows, with more particularity in subsequent sections.

I. General Overview

A first embodiment of the blade changer comprises lower and upper stage bodies 1, 5, respectively. With reference to FIG. 1 the microtome blade cartridges are removably located within the upper stage body 5. The lower stage body is adaptable to a wide variety of rotary microtomes, and serves as the common interface mounting for the upper stage. The disposable blade cartridges 10, 15 are adapted to lock into the upper stage body 5 so as to provide an element of safety. The cartridges are described more fully below and in FIGS. 3–5. They are releasable only when the individual blades are fully secured within the body of the cartridge. This "interlock" function can be attained in many ways, however a preferred embodiment includes an on-board microcontroller which monitors the state of operation of the blade changer. When the controller's logic functions determine that no blade edges are exposed, then the clamping plate and/or the cartridges may be released. The interlock function is more fully described below. The clamping means includes clamping plate 20, support plate 25, and clamp pivot rod 112 which together function to clamp the blade in the cutting position during use of the blade in the microtome. Loading segment 30 has a toothed gear portion rotatably mounted to engage the reciprocal teeth on dispensing tab 90. Dispensing tab 90 is integral with the supply cartridge. At a second end of the supply cartridge loading segment 30 engages loading cam 40 (FIG. 2). The function of loading segment 30 is to move dispensing tab 90 of the blade supply cartridge 15 thereby urging new blades 95 to the central cutting area. This is performed through downwardly protruding member 92 which engages a slot or hole 96 formed in the body of blade 95 (See FIG. 3) which enables dispensing tab 90 to engage the topmost blade in its stored position at the top of the stack of blades contained within supply cartridge 15. Loading cam 40 engages with the lower extending portion 32 of loading segment 30 through the groove in the surface of loading cam 40 thereby enabling rotation of loading segment 30 around shoulder screw 35. Shoulder screw 35 is anchored into upper stage body 5 and its function is to provide a pivot for loading segment 30.

Power means comprises bidirectional DC motor 50 which drives the motor gear 55, which in turn drives the drive shaft gear 60. The purpose of the motor, gear and pulley is to rotate drive shaft 65 and thus provide the power for moving loading segment 30 from left to right, and/or from right to left; and simultaneously moving clamping plate 20 forward and backward in order to either clamp or release a blade in the cutting area. The motor is bidirectional so that clamp pivot rod 112 may be released only when the motor is reversed. This function would require a clutch mechanism that in forward (normal) operation engages a groove in the rod, which stops the rod from being removed from the blade changer. Since removal of the rod is a precursor to removal of the clamping plate for cleaning access, this is another safety interlock feature of the device.

The loading cam 40 and clamping cam 45 are coordinated so that loading segment 30 can only push a new blade 95 into position when clamping plate 20 is open pressure relieved from the blade). It is well within the skill in the art to design and position the two cams to effectuate this coordinated function. Electronic control means includes a printed circuit board 70 which contains the microcontroller and associated circuits and to controls the operation of the blade changer, push-button switches 76, 77 an keypad 75, a power source 85, and safety interlocks 155. The "blade advance" signal comes to the electronic circuit from keypad 75 via blade advance switch 76. In a preferred embodiment the power for the blade changer is supplied from the on-board battery 86. Alternatively, power could be supplied from an AC source (not shown).

Figure 7:
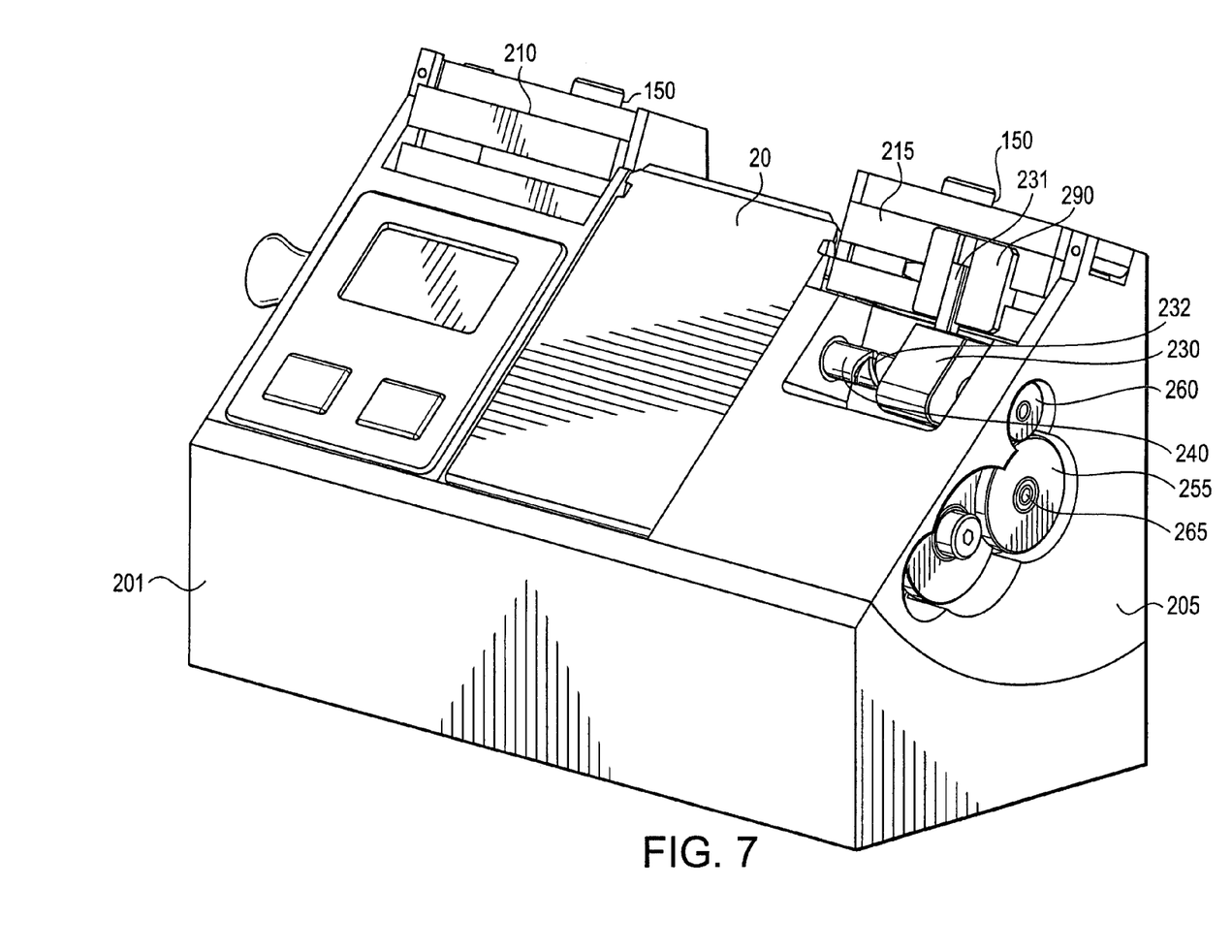
FIG. 7 is a front elevational view of the second embodiment of the automated blade changer with both upper and lower stages shown. A cutout shows the drive shaft gearing arrangement.
Figure 8:
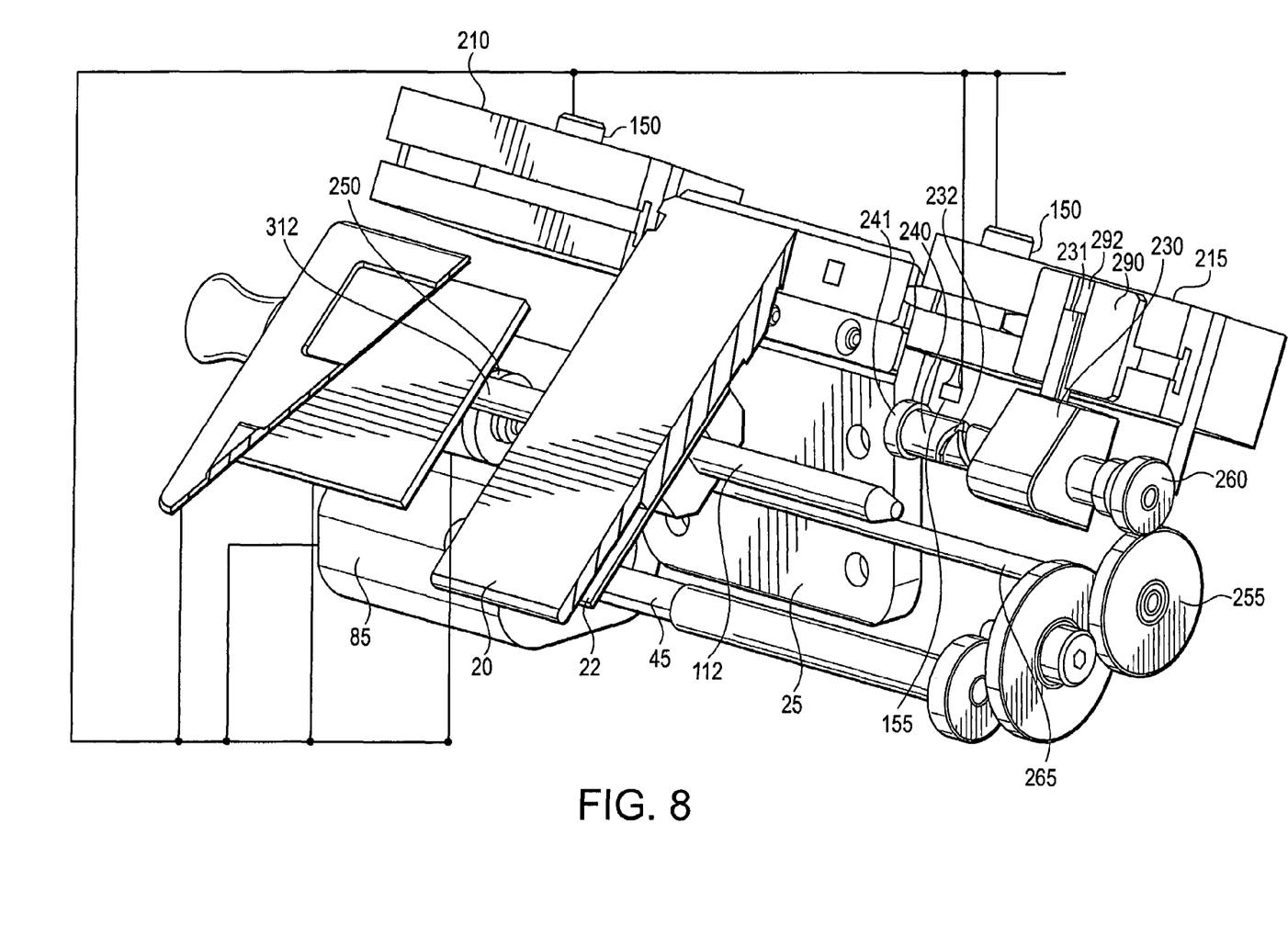
FIG. 8 is a front elevational view of the second embodiment of the automated blade changer with partial cutaway of the upper stage of the device.

A second embodiment of the automated blade changer is depicted in FIGS. 7 and 8. The primary difference in this second embodiment is that loading segment 30 and the attendant gearing for it have been replaced with a reverser screw 240 and reverser shuttle 230 combination. The dispensing tab on the supply cartridge has also been modified to adapt to the shuttle. The advantages include less coordination of the motion because the shuttle reverses direction automatically as the drive shaft continues in a unidirectional fashion II. Detailed Description of the Invention The clamping means includes clamping plate 20, support plate 25, and clamp pivot rod 112 which together function to clamp the blade in the cutting position during use of the blade in the microtome. Support plate 25 has a thin rectangular block 27 attached on its surface which provides a ledge upon which blades in the cutting area sit. In a preferred embodiment, the ledge can be magnetized which aids in retention of the blade on the support plate. Alternatively, a ledge could be machined into its surface to provide the same support function. Clamping cam 45 engages clamping plate 20 on leaf spring 22 so that when the cam is turned, clamping plate 20 releasably engages support plate 25, thus holding or releasing blade 100. A clamp pivot rod 112 provides a pivot point about which the clamp pivots. The rod may pass through a hole or tunnel in the plate or it may be mounted directly behind the plate. In a preferred embodiment, the rod passes through the block 21 securely attached to the plate. The rod is anchored to the upper stage body 5 at both ends through holes adapted for receiving the rod (not shown). Other clamping means come within the spirit and scope of the invention, which are not explicitly taught herein, but which are equivalent in function to those presented herein. For instance, it is possible to use a manual clamp to attain the similar results, albeit with a loss in automation of the entire procedure. Another preferred embodiment would utilize a servo motor directly moving the clamp, replacing clamping cam 45.

Figure 6:
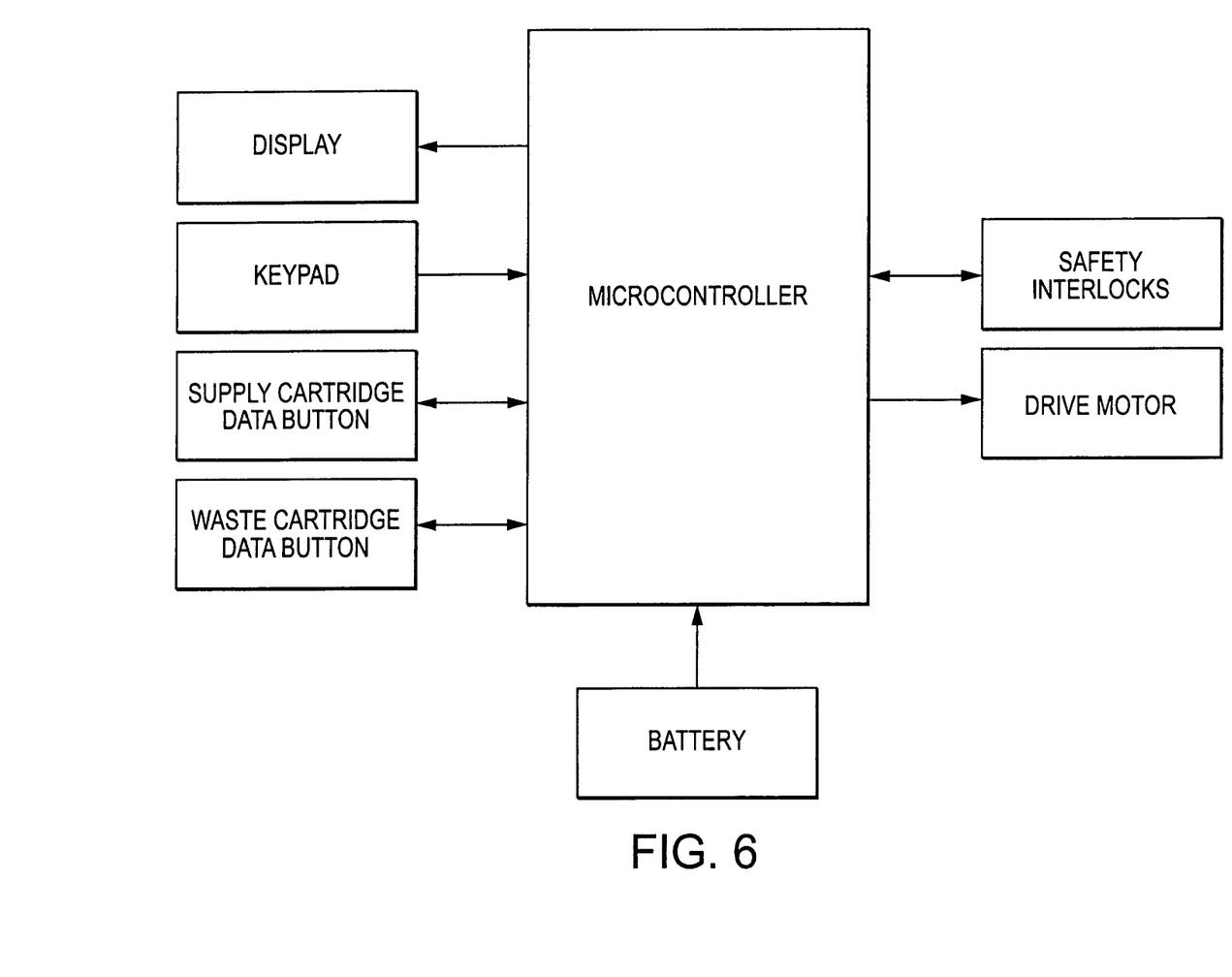
FIG. 6 is a block diagram of the electronics controlling the blade changer.

Electronic control means are depicted schematically in FIG. 6. It includes a printed circuit board 70 (FIG. 2) mounted below the key pad which contains the microcontroller and controls the operation of the blade changer. In a preferred embodiment, the electronic controls are on-board, but alternatively they may be contained in an instrument housing separate from the blade changer. A suitable microcontroller for driving the operations of the blade changer is selected from the PIC family of microcontrollers, manufactured by Microchip, Inc., Chandler, Ariz. One of ordinary skill in the electronic arts is able to select and implement an individual PIC controller for these purposes. The "blade advance" signal comes to the microcontroller circuit from user-activated push-button switch located on keypad 75, also a part of the control means. In a preferred embodiment also the power for the blade changer is supplied from the on-board battery 86. Alternatively, power could be supplied from an AC adapter. The electronic control means also enables the interlock function. The safety interlock feature hardware includes a touch memory device 150 (also known as a "data button") mounted on a blade cartridge, the microcontroller, touch memory reader, and electronically-controlled locking mechanisms for the cartridges 10, 15. The interlock function is described in more detail below.

Disposable microtome blade cartridges are described herein with new and useful advantages. As shown in cross-section C—C (FIG. 3C), supply cartridge 15 comprises a body 105, having sides 110, 115, and a top portion 120 having a groove or slot 125 adapted for receiving rail portion 130 of dispensing tab 90. Sides 110 and 115 each have a guide slot 117 machined into them for engaging cartridge guides 119. In a preferred embodiment the guides are rod-shaped and are mounted to the upper stage and are positioned so that when a cartridge engages the guides it is correctly positioned relative to the support plate 25 and the loading segment 30. Spring 107 is contained within body 105 and serves to urge the blade stack 135 upwardly towards the blade exit 140. Any conventional spring type may be used, including leaf springs, helical springs, and even a spring member integral to the body 105, such as a molded plastic tab. A touch memory device 150 is attached to the cartridge and contains the information pertaining to the contents of the cartridge, such as the number of blades, type, lot number, expiration, and related information. The touch memory device enables communication between the cartridge and the blade changer, thus adding an element of intelligence to the blade changer.

Figure 5A:
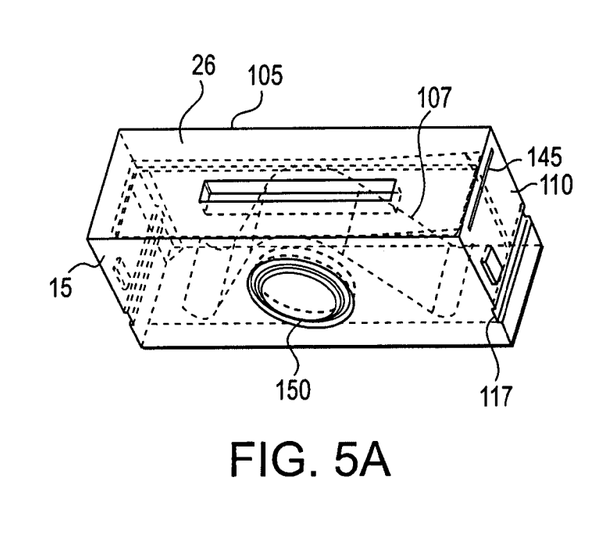
FIGS. 5A–C are, respectively, a front elevational perspective view of a dedicated waste cartridge, a top view of the same, and a sectional view along lines D—D.
Figure 5B:
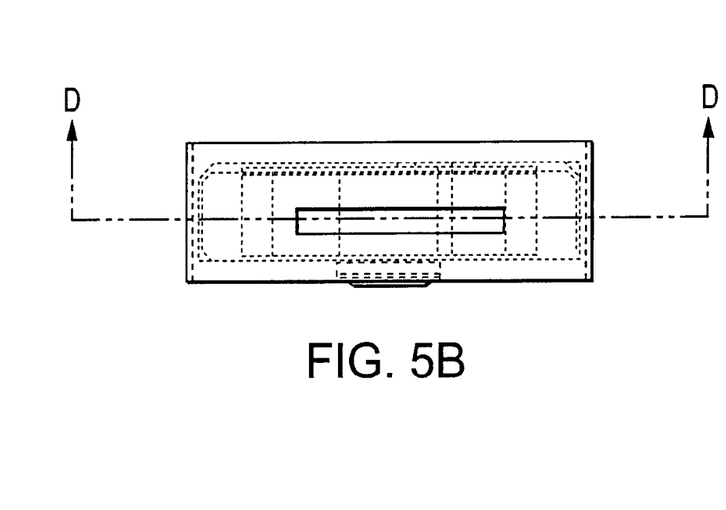
Figure 5C:
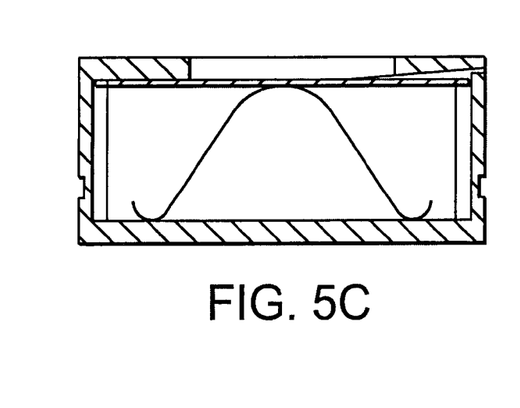

The supply cartridge may also serve to function as a waste cartridge for accepting spent blades. Again with reference to FIG. 3C, cross-section C—C shows an entrance 145 for used blades. The supply cartridge is oriented on upper stage body 5 in reverse so that entrance 145 receives spent blades as they are pushed out of the cutting position by a new blade. As the user continues to load new blades, used blades accumulate in the reversed supply cartridge now functioning as a waste cartridge. Spring 107 will be pushed towards the top 120 of the cartridge as waste blades accumulate. The microcontroller will signal the user that the waste cartridge is filled when the microcontroller has recorded the maximum number of allowable blades. Alternatively, a dedicated waste cartridge is also possible, and is depicted in FIGS. 5A–C.

Again with reference to FIG. 3, supply cartridge 15 has a dispensing tab 90 integral with the cartridge and adapted for engaging each new blade 95. Downward protrusion 92 engages a slot or opening in each new blade. The downward protrusion may be a metal tab, a plastic hook or similar equivalent article. The main design limitation is that it reliably contact only one blade at a time. Downward protrusion 92 may be located anywhere on dispensing tab 90 so long as it functions to urge a single blade out of the cartridge for each cycle of the loading segment 30. In the preferred embodiment shown in FIG. 3, the protrusion is forward mounted on the blade side of dispensing tab 90. A second embodiment of the dispensing tab is shown in FIGS. 7–8.

The primary feature is that dispensing tab shown (290) is designed with a slot or cutout for aging shuttle tab 231. It does not have the teeth necessary for engaging the loading segment 30, which is not present in this embodiment.

The safety interlock feature will now be described with more particularity. The safety interlock feature includes touch memory device 150 mounted on the cartridge (FIGS. 3A–3B, 7–8), an on-board PIC microcontroller contained within the blade changer for running the operations of the device while being in communication with the touch memory device, a contact reader (not shown) for the data button, and electronically-controlled locking mechanisms for the cartridges. The touch memory device is described in U.S. Pat. No. 6,045,759, filed Dec. 19, 1997 and issued Apr. 4, 2000, incorporated herein by reference in its entirety. In a preferred embodiment, the memory device is an EPROM such as the Dallas Semiconductor DS 1985 F5 16 Kbit add-only touch memory device. Its primary function is to initialize the safety interlock system for each new blade cartridge that is presented to the blade changer. The touch memory device contains information such as the number of blades, date of expiration, lot no., etc. In operation, the touch memory device is initially read-in the number of blades in the cartridge when loaded with blades at the factory. When the cartridge is loaded into the supply position on the blade changer, contacts on the cartridge connected to the touch memory device, or the touch memory device itself, make electrical contact with a touch memory reader (not shown) which is built into the upper stage so that as the cartridge seats itself it contacts the touch memory reader. The on-board microcontroller then tracks the position and number of blades left in the cartridge until the cartridge is empty. The on-board microcontroller will then notify the user through an interface such as LEDs or LCD readout. The on-board microcontroller executes the blade loading functions and maintains a look-up table that correlates blade position with steps executed, and so it tracks where the blades are at all times, and most importantly, whether blades are outside of the cartridges (and a potential safety hazard). If they are, then the interlock function will not allow the cartridges to be removed until the blades are within their respective cartridges. Safety interlocks 155 (FIGS. 2, 8) are mechanical- or solenoid-operated latches or arms that retain the cartridge in position, until activated by the microcontroller to release the cartridge A hole or other ledge for the latch to attach to is located on the cartridge on the side facing the upper stage.

The cycle portion of the operation of the blade changer will now be described, with particular reference to FIGS. 2 and 4. Starting with loading a new blade cartridge, a new supply cartridge 15 is loaded into the upper stage body 5, and locks into position. To eject a new blade 95 from supply cartridge 15, the user presses the blade advance push-button 76 on key pad 75. Switch 76 is in electrical communication with the microcontroller which then activates motor 50. Motor 50 actuates driving gear 55 and gear 60 which cause rotation of drive shaft 65. This action then causes the loading and clamping cams 40 and 45, respectively, to move in fixed relation with each other. These cams are oriented on the drive shaft so that the clamping cam 45 is not engaged with the clamping plate 20 for the first half-turn of drive shaft 65 while loading cam 40 is moving loading segment 30 from right to left and consequently dispensing tab 90 moves the first part of the new blade into the cutting area.

During the second half-turn of drive shaft 65 clamping cam 45 engages with clamping plate 20 causing the blade to be clamped in the cutting position while the loading cam 40 moves the loading segment 30 and the dispensing tab 90 from left to right. In the middle of this move the microcontroller stops motor 50 and the blade 95 stays clamped ready for cutting.

Figure 4A:
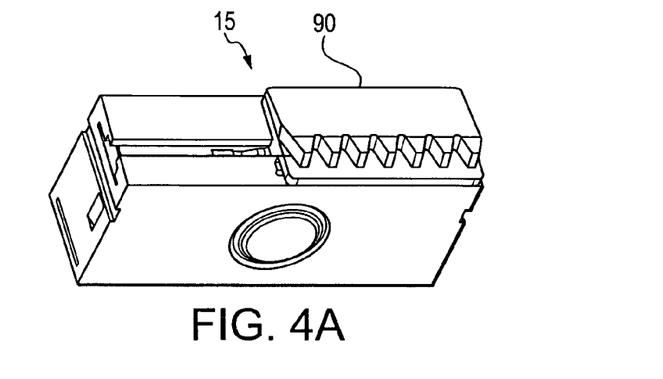
FIGS. 4A–D are front elevational views of the sequence of positions that a blade typically arrives at during loading.
Figure 4B:
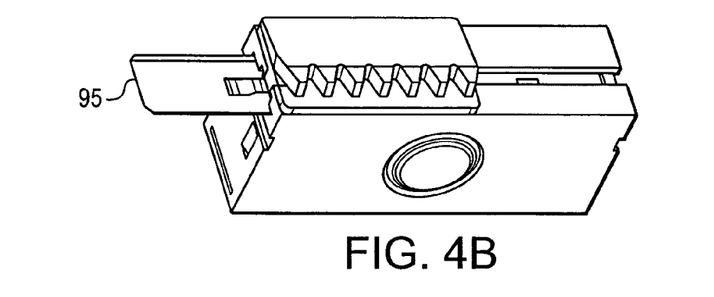
Figure 4C:
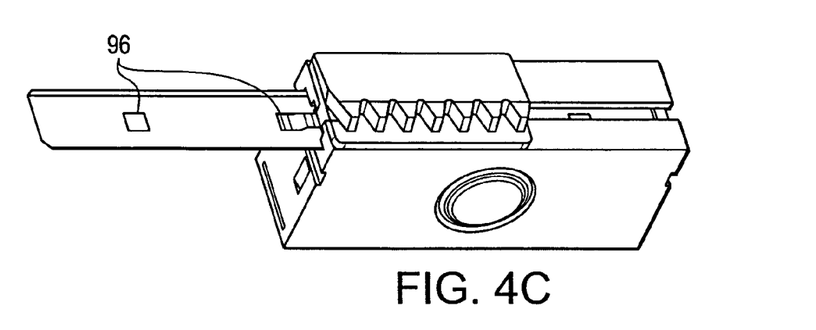
Figure 4D:
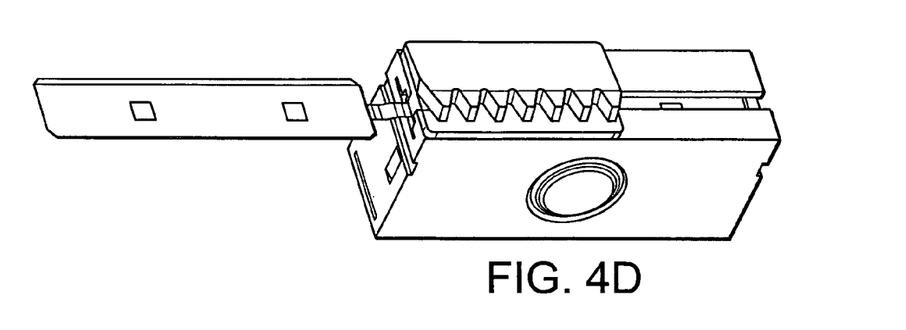

When the new blade 95 is pushed from the supply cartridge 15 to the cutting area it pushes the used blade from the cutting area to waste cartridge 10. This design allows partial movement of the new blade 95 in one direction (⅓ of a blade width with each back-and-forth cycle of the loading segment), in order to maximize use of the blade for small tissue blocks. It takes three full cycles of the dispensing tab to fully eject and position new blade 95. More particularly and with reference to FIGS. 4A–4D, FIG. 4A shows the supply cartridge 15 at rest with the new blade 95 concealed from view within the cartridge (start position). As loading segment 30 (not shown in this view) is activated, it engages the teeth on dispensing tab 90 which then pushes new blade 95 one third of its length out of the housing (FIG. 4B). As loading cam 40 rotates, the direction of dispensing tab 90 is then reversed by loading segment 30, and the tab moves back to its starting position. The second cycle repeats the left-right motion of the dispensing tab, pushing the blade yet another one-third of its length (FIGS. 4C and 4D) per cycle. FIG. 4D shows a fully ejected new blade 95. Clearly an alternative embodiment which pushes the blade out a different fraction of its length, such as ¼, or ⅕, is also within the spirit and scope of this invention.

Referring again to FIG. 2, the used blade 95 is pushed out of its cutting position by the action of the new blade 95 being urged out of the supply cartridge, as previously described. The two blades occupy the same plane, and so as a new blade is ejected, it engages the old blade at their common edges. The used blade is pushed into waste cartridge 10, which may be an empty supply cartridge adapted to fit into upper stage body 5 (FIG. 5), or it may be an empty supply cartridge being reversible and having an entrance 145, as previously described. In an alternate embodiment, a dedicated waste cartridge may be used. In FIGS. 5A–C, such a cartridge is shown. It shares many of the same components as the supply cartridge.

A second embodiment of the blade changer comprises lower and upper stage bodies 201, 205, respectively. With reference to FIGS. 7–8, the microtome blade cartridges are removably located within the upper stage body 205. The lower stage body is adaptable to a wide variety of rotary microtomes, and serves as the common interface mounting for the upper stage. The disposable blade cartridges 210, 215 are adapted to lock into the upper stage body 205 so as to provide an element of safety. The cartridges are described more fully in the first embodiment and in FIGS. 3–5. In this second embodiment they differ only in that the dispensing tab 90 (FIGS. 1–2) is replaced by dispensing tab 290 (FIGS. 7–8). The cartridges are releasable only when the individual blades are fully secured within the body of the cartridge. This "interlock" function can be attained in many ways, however a preferred embodiment includes an on-board microcontroller which monitors the state of operation of the blade changer. When the controller's logic functions determine that no blade edges are exposed, then the clamping plate and/or the cartridges may be released. The interlock function is more fully described below. The clamping means includes clamping plate 20, support plate 25, and clamp pivot rod 112 which together function to clamp the blade in the cutting position during use of the blade in the microtome. Reverser shuttle 230 has a shuttle tab portion 231 mounted to engage the slot 292 in dispensing tab 290. Dispensing tab 290 is integral with the supply cartridge 215. Reverser shuttle 230 has a threaded portion (not shown) which engages reverser screw 240. The function of reverser shuttle 230 is to move dispensing tab 290 of the blade supply cartridge 215 thereby urging new blades 95 to the central cutting area. As shown by FIGS. 3–4, this is performed through downwardly protruding member 92 which engages a slot or hole 96 formed in the body of blade 95 which enables dispensing tab 290 to engage the topmost blade in its stored position at the top of the stack of blades contained within supply cartridge 215. Reverser screw 240 is supported on either end by bearings 241 which are supported and retained by upper stage body 205. Reverser shuttle 230 engages reverser screw 240 through helical cutout 232 and mating helical threads (not shown) located on the shuttle 230. In a preferred embodiment, reverser shuttle 230 acts like a threaded nut and moves laterally at the urging of reverser screw 230. The helical cutout of reverser screw 230 is unique in that the reverser shuttle will move back and forth without a concomitant change in direction of any other component in the drive train. Similar reverser screws are common and well-known in the ink-jet printer art.

Power means comprises bidirectional DC motor 250 which rotates drive shaft 265 and drive gear 255, which in turn engages reverser screw gear 260. Reverser screw gear 260 in turn is attached to reverser screw 240, and when rotational motion is applied through drive shaft 265 the result is rotational motion in reverser screw 240, and thus the threads of reverser shuttle 230 will be urged to move laterally along the helical cutout. Drive shaft 265 also simultaneously moves clamping plate 20 forward and backward in order to either clamp or release a blade in the cutting area. The motor is bidirectional so that clamp pivot rod 112 may be released only when the motor is reversed. This function would require a clutch mechanism that in forward (normal) operation engages a groove in the rod, which stops the rod from being removed from the blade changer. Since removal of the rod is a precursor to removal of the clamping plate for cleaning access, this is another safety interlock feature of the device.

The reverser screw 240 and clamping cam 45 are coordinated so that reverser shuttle 230 can only push a new blade 95 into position when clamping plate 20 is open (pressure relieved from the blade). It is well within the skill in the art to design and position the two cams to effectuate this coordinated function.

The functional advantages of the invention described above are numerous. First, the blades are moved into the cutting area completely without manual contact. Second, blades are moved into the waste cartridge for disposal completely without manual contact. Third, moving the blades automatically, by push-button switch or by manual lever, is a fast, efficient way to load and unload.

Although certain presently preferred embodiments of the invention have been described herein, it will be apparent to those skilled in the art to which the invention pertains that variations and modifications of the described embodiment may be made without departing from the spirit and scope of the invention. Accordingly, it is intended that the invention be limited only to the extent required by the appended claims and the applicable rules of law.

We claim:

1. An automated rotary microtome blade changing apparatus, comprising (a) an upper stage adapted to releasably engage a supply and a waste cartridge, said tipper stage including a loading segment adapted to engage and move blades contained within said supply cartridge into a cutting position;

(b) means for releasably clamping said blades in place for cutting operations, comprising a fixed support plate adapted to support a first side of said blade, said fixed support plate in intimate contact with the upper stage body, a clamping plate having a clamping surface capable of engaging a second side of said blade when the clamping plate is pivoted into the clamping position, a pivot means for supporting a midpoint region of said clamping plate, said pivot means itself being integral to or supported by said upper stage, a clamping cam that engages said clamping plate, said clamping cam being mounted on a drive shaft and providing motion orthogonal to said drive shaft axis thereby pivoting the clamping plate about said pivot point;

(c) means for powering the movement of blades and clamping mechanisms, comprising an electric motor mounted proximate to said drive shaft, a motor pulley mounted between said drive shaft and said electric motor and interconnected therebetween so that power from said motor is transferred to said drive shaft; and (d) means for electronically controlling all of the functions of the apparatus, comprising a microcontroller in electrical communication with a keypad, a power source, a motor, safety interlocks, a display, and data buttons for both waste and supply cartridges.

2. An automated rotary microtome blade changing apparatus, comprising (a) an upper stage adapted to releasably engage a supply and a waste cartridge, said upper stage including a reverser shuttle adapted to engage and move blades contained within said supply cartridge into a cutting position;

(b) means for releasably clamping said blades in place for cutting operations, comprising a fixed support plate adapted to support a first side of said blade, said fixed support plate in intimate contact with the upper stage body, a clamping plate having a clamping surface capable of engaging a second side of said blade when the clamping plate is pivoted into the clamping position, a pivot means for supporting a midpoint region of said clamping plate, said pivot means itself being integral to or supported by said upper stage, a clamping cam that engages said clamping plate, said clamping cam being mounted on a drive shaft and providing motion orthogonal to said drive shaft axis thereby pivoting said clamping plate about said pivot point;

(c) means for powering the movement of blades and clamping mechanisms, comprising an electric motor adapted to engage said drive shaft, a drive gear mounted on said drive shaft, said drive gear transmitting power to said clamping means and said reverser shuttle; and (d) means for electronically controlling all of the functions of the apparatus, comprising a microcontroller in electrical communication with a keypad, a power source, said motor, safety interlocks, a display, and data buttons for both waste and supply cartridges.

* * * * *